US00PP09410P

United States Patent [19]

DeRoose et al.

[11] Patent Number: Plant 9,410

[45] Date of Patent: Dec. 26, 1995

[54] VRIESEA PLANT NAMED 'BARBARA'

[75] Inventors: Reginald DeRoose, Drootge 139, 9940 Evergem, Belgium; Nico J. Kuipers, De Kwakel, Netherlands

[73] Assignee: Reginald DeRoose, Evergem, Belgium

[21] Appl. No.: 374,297

[22] Filed: Jan. 18, 1995

[51] Int. Cl.[6] ..... A01H 5/00

[52] U.S. Cl. ..... Plt./88.8

[58] Field of Search ..... Plt./88.8

*Primary Examiner*—James R. Feyrer

*Attorney, Agent, or Firm*—Foley & Lardner

[57] ABSTRACT

A new and distinct cultivar of Vriesea plant named Barbara, particularly characterized by its very large inflorescence relative to the size of the plant, floral bracts which are bright red, thick and umbricate, and its compound inflorescence of 8–10 branches each of which is up to 20 cm in length.

1 Drawing Sheet

The present invention comprises a new and distinct cultivar of Vriesea, botanically known as *Vriesea poelmanii,* and referred to by the cultivar name Barbara.

The new cultivar is a product of a planned breeding program carried out by inventor Reginald Deroose in Evergem, Belgium. The male and female parents used in the original cross are not known at this time.

Seedlings were mass-selected from the original cross and grown out. These seedlings were asexually propagated by tissue culture by Reginald Derosse in Evergem, Belgium to increase the population and were grown out to flower in controlled environments in Evergem, Belgium and De Kwakel, The Netherlands. Of the plants flowering in De Kwakel, the new cultivar was discovered and selected by inventor Nico J. Kuipers in 1989.

Subsequent asexual reproduction in Evergem, Belgium by tissue culture, performed by inventor Reginald Deroose, has demonstrated that the combination of characteristics as herein disclosed for the new cultivar are firmly fixed and are retained through successive generations of asexual reproduction.

The following traits have been repeatedly observed and in combination distinguish Barbara as a new and distinct cultivar.

1. The total inflorescence is very large in comparison with the shape of the plant.

2. The leaves are in a dense rosette, with the leaves extending generally erect, and total plant diameter being approximately 55 to 60 cm.

3. The compound inflorescence contains 8 to 10 branches, which are 15 to 20 cm long. The branches are in an angle of about 45° with the main stem.

4. The floral bracts are bright red, thick and umbricate.

The accompanying color photographic drawings illustrate the features of the new cultivar, with colors being as accurate as possible with color illustrations of this type. The top photograph shows an entire plant of Barbara in full bloom. The bottom photo is an enlarged showing of the inflorescence, showing the same in greater detail.

The new cultivar can be generally compared to other plants of the same species. Barbara is similar to other plants with respect to the shape and color of the inflorescence, and the general outlook of the plant. Barbara is distinguished from other plants of the species by its slightly larger size, more erect leaves, more branches in its inflorescence, and its larger inflorescence.

The following observations, measurements and values describe plants grown in De Kwakel, The Netherlands under greenhouse conditions which closely approximate those generally used in horticultural practices. Color references are made to The Royal Horticultural Society (R.H.S.) Colour Chart, except where general color terms of ordinary significance are used. The color values were determined between 1:00 and 3:00 p.m. on Oct. 29, 1993 under slightly cloudy daylight conditions at De Kwakel, The Netherlands.

Classification: *Vriesea poelmanii* cv. Barbara.

Parentage:

*Male parent.*—Unknown.

*Female parent.*—Unknown. The cultivar originated from a mass selection of seedlings from a cross between unknown parents of *Vriesea poelmanii.*

Propagation: Asexual propagation by tissue culture.

Plant: About 45 cm tall when grown in 13 cm pot, and approximately 55 to 60 cm in diameter when fully grown. Has excellent growth habit and is very vigorous.

Leaves:

*Shape.*—Oblong with tips bending down.

*Size.*—Length: 35 to 45 cm. Width: 3.5 to 4.5 cm at the middle and 9, 5 cm at tip.

*Margin.*—Entire.

*Surface texture.*—Glabrous.

*Veins or ribs.*—Slightly visible on upper surface; visible on lower surface.

*Color.*—Upper surface: Closest to 137A but slightly darker. Lower surface: 146A.

Inflorescence:

*Bracts.*—Scape: Erect, total length about 30 cm, 1.5 to 2 cm in diameter, main stem with 8 to 10 branches each of which is up to 20 cm in length; color approximately 45A.

*Bract shape.*Oval (see photo).

*Bract size.*—3 to 4 cm long, alternately arranged.

*Total bract height.*—About 20 cm.

*Number of bracts.*—8 to 10.

*Color.*—Approximately 45A.

*Flowers.*—Typical, borne at and extending outwardly of floral bracts, one flower per bract; flowering normally in progression from base to tip of scrape or bracts, with many flowers blooming at same time. Main color 17A.

*Duration of flower.*—After bud is visible, approximately 6 weeks are required for inflorescence to extend and develop. Floral bracts start to show little yellow flowers. The inflorescence color remains for 4 months.

Reproduction organs:

*Stamens.*—One (1) per flower, color 2A.

*Pistils.*—Six (6) per flower, color 17A.

Resistance to diseases: No disease problems noted to date.

It is claimed:

1. A new and distinct cultivar of Vriesea plant named Barbara, as illustrated and described.

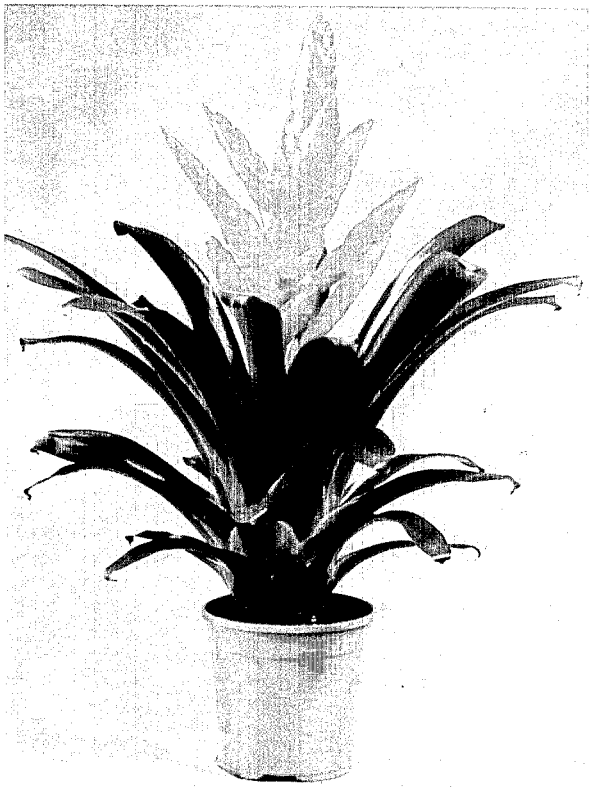
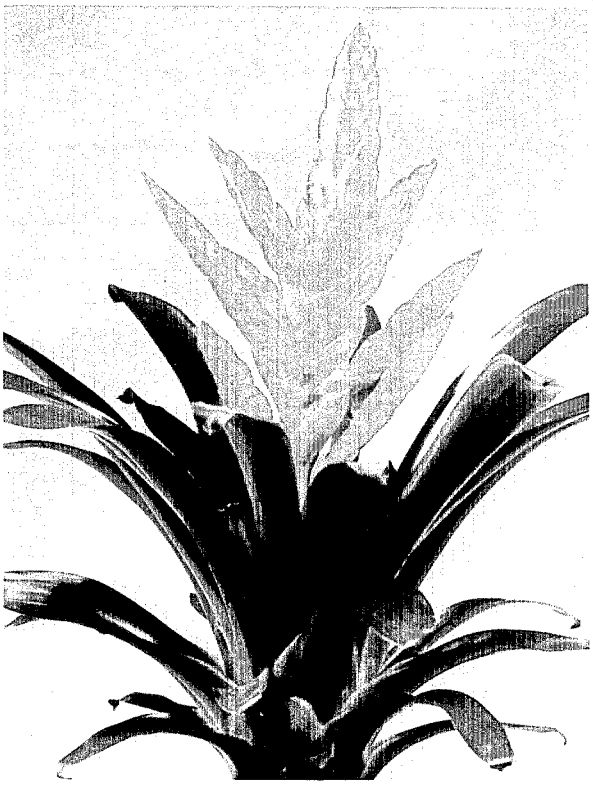

* * * * *